United States Patent
Huffman et al.

[19]

[11] Patent Number: 5,887,118
[45] Date of Patent: Mar. 23, 1999

[54] OLFACTORY CARD

[75] Inventors: James Robert Huffman, Austin, Tex.; Ronald Dale Cruickshank, Durham, N.C.; Shrirang Nikanth Jambhekar, Schaumburg, Ill.; Jeffrey Van Myers, Driftwood; Russell Lawrence Collins, Austin, both of Tex.

[73] Assignee: Motorola, Inc., Schaumburg, Ill.

[21] Appl. No.: 799,739

[22] Filed: Feb. 12, 1997

[51] Int. Cl.[6] ............................ A61M 16/00; H05K 5/00
[52] U.S. Cl. ............................ 392/390; 361/683
[58] Field of Search ................................ 392/386, 390; 361/683–686, 736, 737, 738

[56] References Cited

U.S. PATENT DOCUMENTS

| | | | |
|---|---|---|---|
| 4,629,604 | 12/1986 | Spector | 422/124 |
| 4,795,883 | 1/1989 | Glucksman et al. | 392/390 |
| 4,849,606 | 7/1989 | Martens, III et al. | 392/390 |
| 5,115,975 | 5/1992 | Shilling | 239/55 |
| 5,155,663 | 10/1992 | Harase | 361/395 |
| 5,661,635 | 8/1997 | Huffman et al. | 361/684 |
| 5,724,256 | 3/1998 | Lee et al. | 364/502 |

*Primary Examiner*—Teresa Walberg
*Assistant Examiner*—Sam Paik
*Attorney, Agent, or Firm*—S. Kevin Pickens

[57] ABSTRACT

An olfactory card (10) comprises a PC card housing (12) and a PC card connector (14) supported by the PC card housing (12). The olfactory card (10) includes a scent-producing member (20) and an electrical component (24) to activate the scent-producing member (20).

19 Claims, 4 Drawing Sheets

OLFACTORY CARD

RELATED APPLICATION

The present application is related to the following application which is assigned to the same assignee as the present application:

"Reusable Housing and Memory Card Therefor", having Ser. No. 08/572,413, filed Dec. 14, 1995.

The subject matter of the above-identified application is hereby incorporated by reference into the disclosure of this application.

TECHNICAL FIELD

The present invention relates to interface cards for personal computers and like electronic devices.

BACKGROUND OF THE INVENTION

Various types of electronic devices, including personal computers, personal digital assistants, and the like, include a card-receiving slot and an interface for installing a peripheral. An example of such is a PCMCIA (Personal Computer Memory Card International Association) socket present in many laptop computers.

Various types of peripherals are available in the form of a PCMCIA card. Examples of such peripherals include modems, memory cards, and hard drives.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Figure 1:
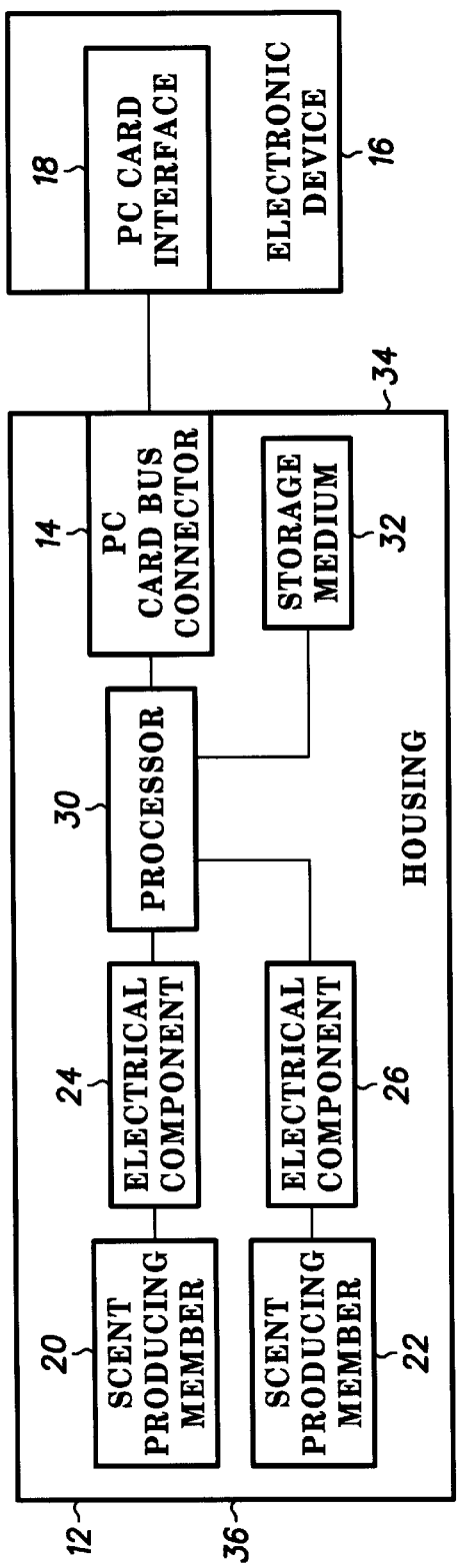
FIG. 1 is a block diagram of an embodiment of an olfactory card in accordance with the present invention.

FIG. 1 is a block diagram of an embodiment of an olfactory card 10 in accordance with the present invention. The olfactory card 10 includes a PC (personal computer) card housing 12. Preferably, the PC card housing 12 is shaped and sized in accordance with a PCMCIA (Personal Computer Memory Card International Association) standard. Examples of PCMCIA form standards include Type I having a thickness of 3.3 mm, Type II having a thickness of 5.0 mm, and Type III having a thickness of 10.5 mm. Independent of the type, it is preferred that the length of PC card housing 12 be 85.6 mm and the width be 54.0 mm in accordance with PCMCIA standards.

The olfactory card 10 further includes a PC card bus connector 14. The PC card bus connector 14 is utilized to interface the olfactory card 10 to an electronic device 16. The electronic device 16 includes a socket into which the olfactory card 10 is inserted. Within the socket is a PC card interface 18 which mates with the PC card bus connector 14.

In PCMCIA embodiments, the PC card bus connector 14 can include 68 connectors which mate with 68 pins included in the PC card interface 18. Here, the PC card bus connector 14 can communicate signals with the PC card interface 18 in accordance with PCMCIA signal standards. In general, however, the PC card bus connector 14 can include any plurality of connectors which mate with an associated plurality of connectors in the PC card interface 18, and can utilize any signal standard.

Examples of the electronic device 16 include, but are not limited to, a personal computer, a portable wireless device, a personal digital assistant, a network computer, a network television, an Internet television, a web television, and a digital book. A preferred form of the digital book is described in the copending application entitled "REUSABLE HOUSING AND MEMORY CARD THEREFORE" incorporated by reference into the disclosure of the present application. Regardless of its form, the electronic device 16 typically includes at least one input device, a processor, a memory, at least one storage device, and a display device. The at least one input device can include a keyboard, a pointing device, and/or a touchscreen for receiving commands from an end user. The at least one storage device can include a floppy disk drive, an optical drive, a CD recordable drive, a DVD drive, or a hard disk drive to store computer readable data. The display device can include a computer monitor, such as an LCD (liquid crystal display) or a CRT (cathode ray tube) display, or a television.

The olfactory card 10 includes at least one scent-producing member, such as a first scent-producing member 20 and a second scent-producing member 22. Each of the at least one scent-producing member is independently activated using a corresponding at least one electrical component. As illustrated, a first electrical component 24 is utilized to activate the first scent-producing member 20 in response to an electrical signal applied thereto, and a second electrical component 26 is utilized to activate the second scent-producing member 22 in response to an electrical signal applied thereto. Here, if desired, the at least one scent-producing member can be activated one-at-a-time, or more than one scent-producing member can be simultaneously activated.

In a preferred embodiment, each of the at least one scent-producing member is heat-activated, such as those utilized in plug-in deodorizers. Here, each of the at least one electrical component is utilized to supply heat to activate its associated scent-producing member. Examples of the at least one electrical component include, but are not limited to, a thick-film heating element, a thin-film heating element, a resistor, and a device having a semiconductor junction such as a diode or a transistor. These electrical components can be selectively heated by applying a voltage or a current across two terminals.

Optionally, the olfactory card 10 includes a processor 30 in communication with the PC card bus connector 14, the first electrical component 24, and the second electrical component 26. The processor 30 is utilized to selectively activate and de-activate the at least one scent-producing member by selectively applying an electrical signal to the at least one electrical component. Here, the processor 30 can autonomously activate and de-activate the at least one scent-producing member with respect to the electronic device 16.

Alternatively, the at least one electrical component is responsive to signals received along the PC card bus connector 14. Here, for example, the at least one electrical component can communicate directly with the PC card bus connector 14 without requiring the processor 30. In this case, the electronic device 16 can control the activation and de-activation of the at least one scent-producing member.

The olfactory card 10 can further include a storage medium 32 in communication with the PC card bus connector 14. The storage medium 32 contains machine-readable data representative of textual information, graphical information, and/or audible information which corresponds to the scents of the at least one scent-producing member. Examples of the storage medium 32 include, but are not limited to, a memory, an optical storage medium, and a magnetic storage medium. The storage medium 32 can directly communicate via the PC card bus connector 14, or can communicate with the processor 30.

The machine-readable data can be representative of textual, graphical, and audible information from a book. It is noted that the term "book" should be construed broadly as any written or printed composition having textual information which is read by an individual. Hence, the term "book" should be inclusive of books, magazines, newspapers, on-line documents such as HTML pages, or the like.

The textual, graphical, and audible information can be encoded in a number of ways for storage by the storage medium 32. In a first embodiment, ASCII data representative of the textual information is stored by the storage medium 32. In a second embodiment, compressed data representative of the textual information is stored. Here, for example, a series of pointers which point to words contained in a prestored dictionary can be stored by the storage medium 32 as described in the copending application entitled "REUSABLE HOUSING AND MEMORY CARD THEREFORE". Further, the storage medium 32 can include any of the control codes described in the aforementioned copending application.

It is preferred that the olfactory information be encoded to correspond to predetermined words or predetermined locations in the book. Here, for example, the storage medium 32 can *include a code that indicates which of the at least one scent-producing member to activate, and a time to activate each scent-producing member.

The PC card bus connector 14, the first scent-producing member 20, the second scent-producing member 22, the first electrical component 24, the second electrical component 26, the processor 30, and the storage medium 32 are all housed and/or supported by the PC card housing 12. The PC card bus connector 14 is externally accessible at a first end 34 of the olfactory card 10. The at least one scent-producing member is located proximate to a second end 36 of the olfactory card 10. Preferably, the second end 36 is opposite to the first end 34. Proximate to the second end 36, the PC card housing 12 can include at least one opening (not specifically illustrated) which allows a scent produced by the at least one scent-producing member to emanate from the olfactory card 10 to an external environment.

Figure 2:
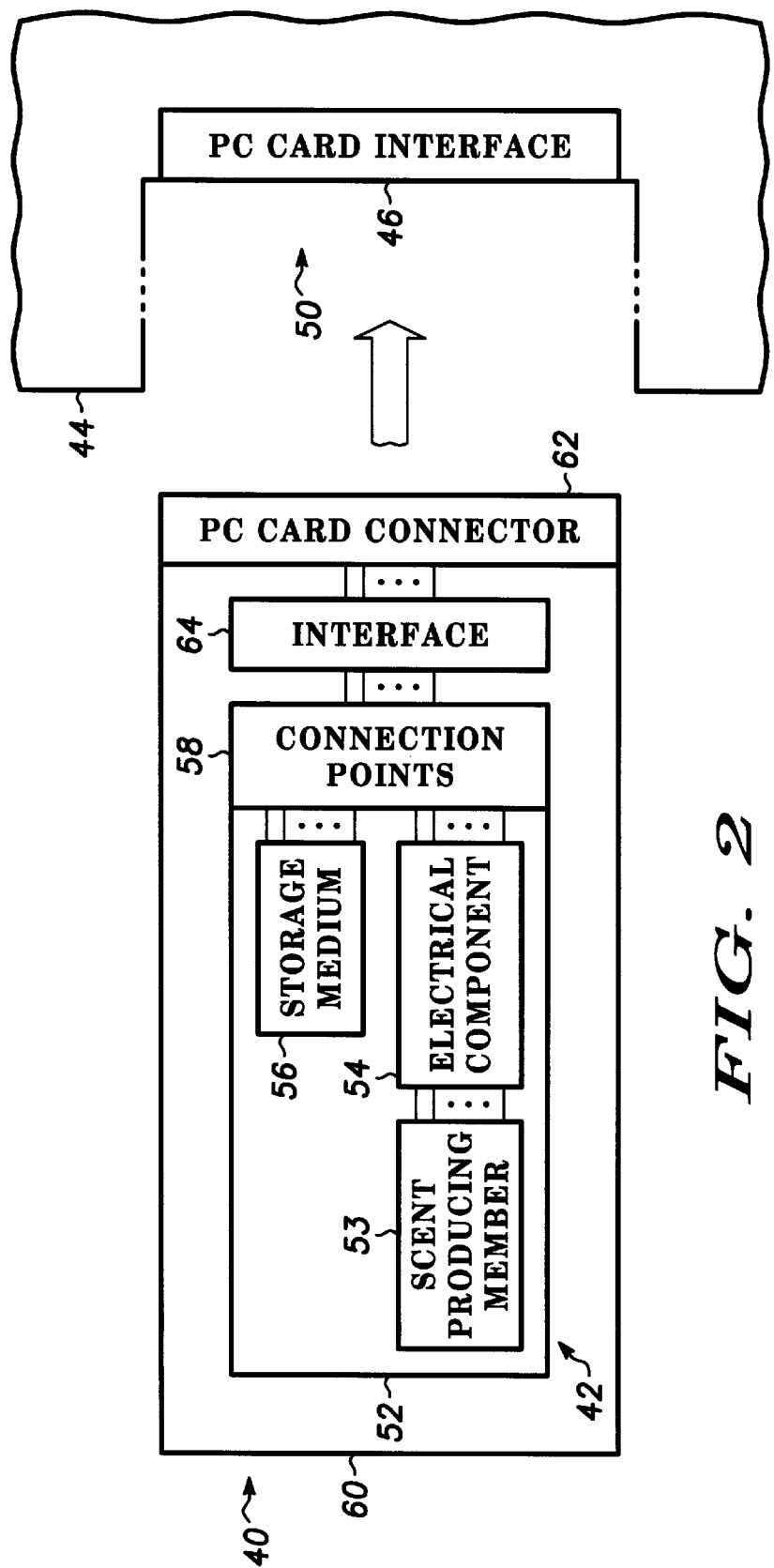
FIG. 2 is a block diagram of a reusable housing for receiving an olfactory card to interface with a device having a PC card interface within a PC card slot.

FIG. 2 is a block diagram of a reusable housing 40 for receiving an olfactory card 42 to interface with a device 44 having a PC card interface 46 within a PC card slot 50. The device 44 can be an electronic book as described in the aforementioned copending application, wherein the olfactory card 42 contains machine-readable data representative of pages of a book.

The olfactory card 42 has a substrate 52 shaped to be removably housed within the removable housing 40. Preferably, the substrate 52 has a thin, card-like form. At least one scent-producing member 53 is supported by the substrate 52. Further supported by the substrate 52 is at least one electrical component 54 to independently and selectively activate each of the at least one scent-producing member 53.

The substrate 52 also supports a machine-readable storage medium 56. The machine-readable storage medium 56 is utilized to store machine-readable data, such as the data representative of pages from a book. A plurality of connection points 58 are supported by the substrate to facilitate external access and communication with the at least one electrical component 54 and the machine-readable storage medium 56.

The reusable housing 40 includes a housing member 60 which removably receives and retains the olfactory card 42. The housing member 60 has an exterior dimensioned to allow insertion thereof in the PC card slot 50. For a PCMCIA card slot, the housing member 60 is dimensioned in accordance with a PCMCIA card dimension.

The reusable housing further includes a PC card connector 62 positioned at an end of the housing member 60. The PC card connector 62 interfaces with the PC card interface 46 when the housing member 60 is inserted in the PC card slot 50. For a PCMCIA interface, the PC card connector 62 includes a PCMCIA connector.

An interface 64 within the reusable housing 40 receives the plurality of connection points 58 when the olfactory card 42 is received by the housing member 60. The interface 64 connects the plurality of connection points 58 to the PC card connector 62 to facilitate communication of the PC card interface 46 with the at least one electrical component 54 and the machine-readable storage medium 56.

Figure 3:
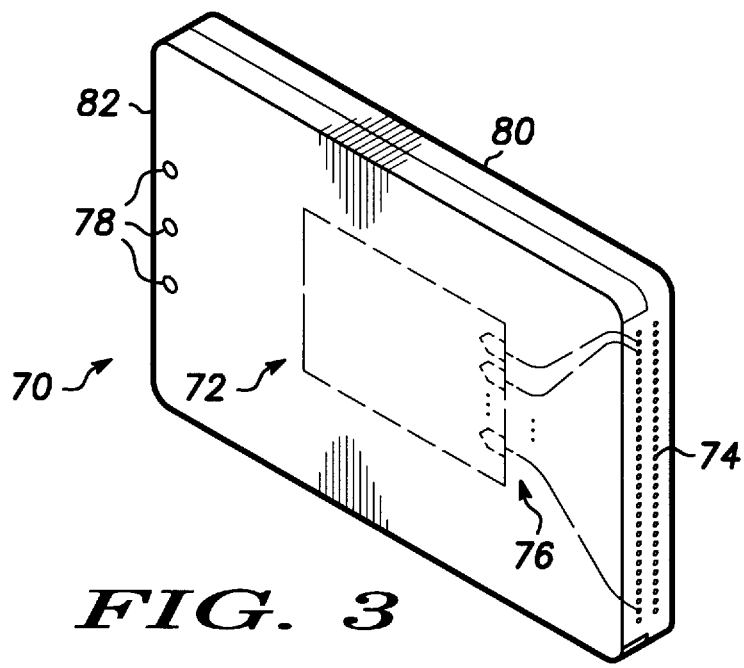
FIG. 3 shows a view of a PCMCIA embodiment of a reusable housing which receives an olfactory card.

FIG. 3 shows a view of a PCMCIA embodiment of a reusable housing 70 which receives an olfactory card 72. The reusable housing 70 includes a PCMCIA card connector 74 which is interfaced to a plurality of connection points 76 of the olfactory card 72. At an opposite end, the reusable housing 70 defines a plurality of openings 78 to allow scents to emanate from the olfactory card 72 to an external environment.

The reusable housing 70 includes a housing member formed by a first clam shell member 80 and a second claim shell member 82. The first clam shell member 80 at least partially disconnects from the second clam shell member 82 to allow an insertion of the olfactory card 72. For example, the first claim shell member 80 can be pivotably connected to the second clam shell member 82, or can completely disconnect from the second clam shell member 82. The first clam shell member 80 can then be reconnected to the second clam shell member 82 to enclose the olfactory card 72.

Figure 4:
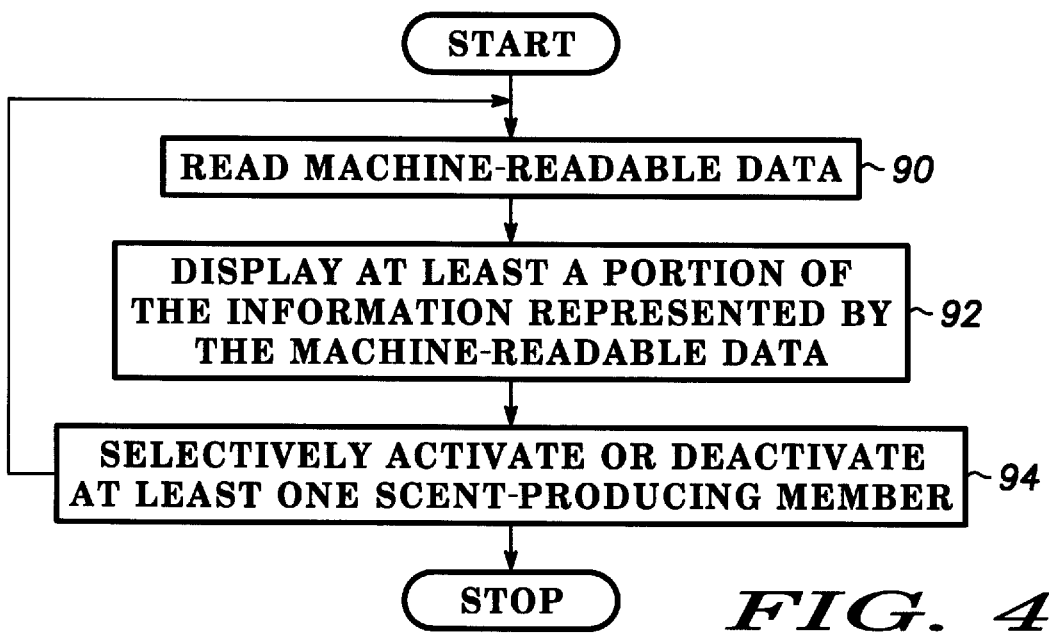
FIG. 4 is a flow chart of an embodiment of a method of using an olfactory card in accordance with the present invention.

FIG. 4 is a flow chart of an embodiment of a method of using an olfactory card in accordance with the present invention. As indicated by block 90, the method includes a step of reading machine-readable data from the olfactory card. The machine-readable data, which is stored by the storage medium 32, can be read by the electronic device 16.

The machine-readable data is communicated to the electronic device 16 via the PC card bus connector 14. The machine-readable data can include textual information, graphical information, and audible information which is to be displayed by the electronic device 16.

As indicated by block 92, the method includes a step of displaying at least a portion of the machine-readable data. This step can include displaying the textual information and the graphical information using a display associated with the electronic device, and/or displaying the audible information using a sound card and a speaker coupled thereto.

Figure 5:
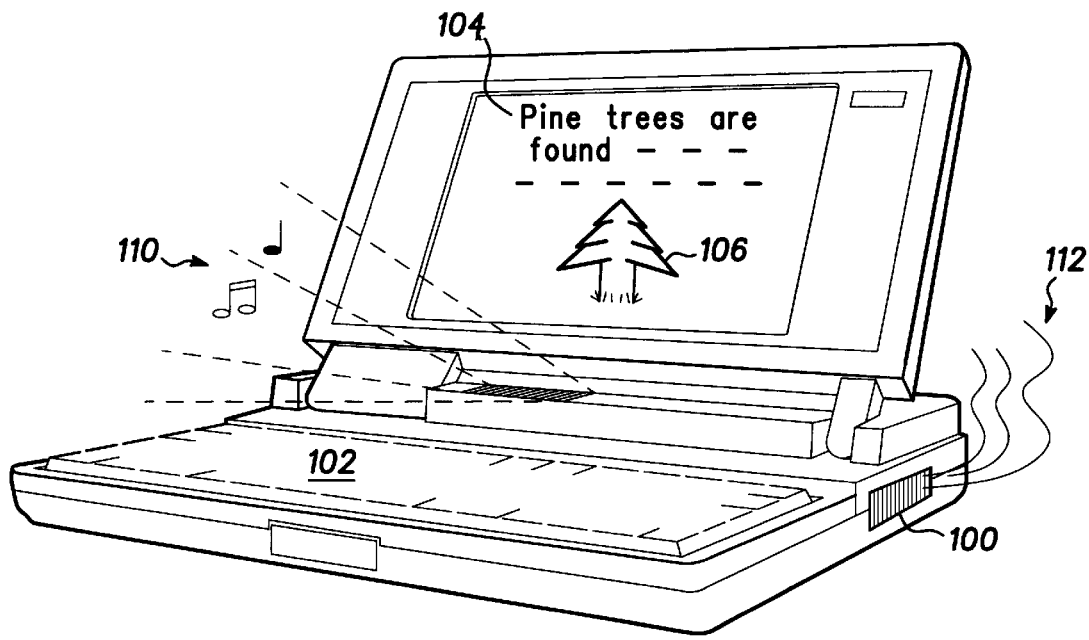
FIG. 5 illustrates an example of an electronic device using an olfactory card.

FIG. 5 illustrates an example of an electronic device using an olfactory card 100. In this example, the electronic device has the form of a laptop computer 102 having the olfactory card 100 inserted into its PCMCIA card-receiving slot.

Upon receiving the machine-readable data read in the step indicated by block 90, the laptop computer 102 displays textual information 104, graphical information 106, and audible information 110. In this example, the textual information 104 provides information about pine trees, the graphical information 106 provides an image of a pine tree, and the audible information 110 can include sounds from a forest or spoken information about pine trees.

Referring back to FIG. 4, the method includes a step of selectively activating or deactivating at least one scent-producing member within the olfactory card, as indicated by block 94. In the case of activating a scent-producing member, it is preferred that the scent emanated thereby be associated with at least one of the textual information, the graphical information, and the audible information. The scent-producing member can be activated for a predetermined time duration, after which the scent-producing member is de-activated. Alternatively, the scent-producing member can be activated until a subsequent page of information is displayed.

Turning back to FIG. 5, the olfactory card 100 interfaced to the laptop computer 102 is shown to emanate a scent 112. For the displayed information pertaining to pine trees, for example, the scent 112 can be a scent of pine trees or a scent of a forest.

Referring back to FIG. 4, the steps indicated by blocks 90, 92, and 94 can be repeated. Here, for example, a subsequent page of information can be read and displayed with all of the scent-producing members in the olfactory card being de-activated. For purposes of illustration, the subsequent page can provide information pertaining to birds having no scents associated therewith in the olfactory card.

Continuing with this example, a further subsequent page of information can be read and displayed, and another scent-producing member can be activated. Here, for example, the laptop computer 102 can read and display information about flowers, and the olfactory card can emanate a flower scent.

Figure 6:
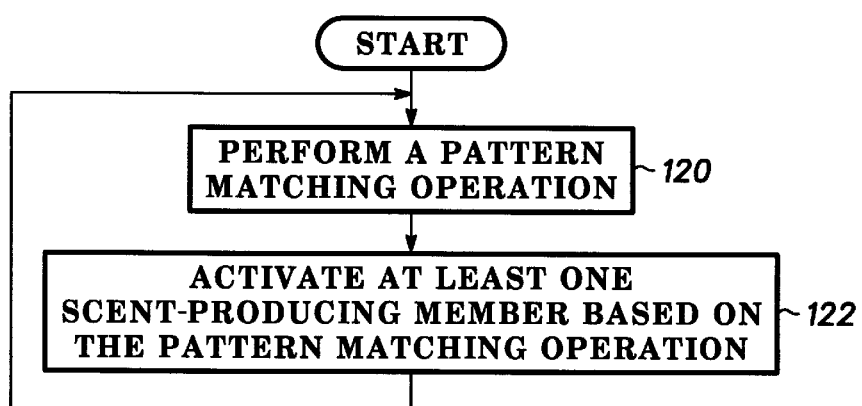
FIG. 6 is a flow chart of another embodiment of a method of using an olfactory card in accordance with the present invention.

FIG. 6 is a flow chart of another embodiment of a method of using an olfactory card in accordance with the present invention. As indicated by block 120, the method includes a step of performing a pattern matching operation to a set of textual information. The pattern matching operation is performed to detect any of a plurality of predetermined words or phrases within the textual information.

As indicated by block 122, the method includes a step of selectively activating at least one scent-producing member based on the pattern matching operation. For example, if the pattern matching operation detects the word "flower" in the textual information, a flower-scent-producing member can be activated. If the pattern matching operation detects the phrase "pine tree" in the textual information, a pine-tree-scent-producing member can be activated.

Figure 7:
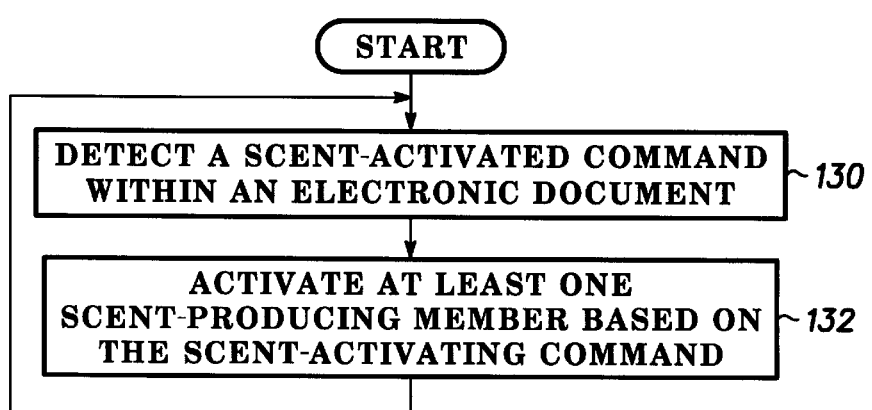
FIG. 7 is a flow chart of a further embodiment of a method of using an olfactory card in accordance with the present invention.

FIG. 7 is a flow chart of a further embodiment of a method of using an olfactory card in accordance with the present invention. As indicated by block 130, the method includes a step of detecting a scent-activating command embedded within an electronic document. The electronic document can include textual information or graphical information associated with the desired scent to be produced. For example, the electronic document can include an HTML (hyper text marking language) document having an embedded HTML command dedicated to scent activation. The HTML document can be downloaded from an electronic network such as the Internet or an intranet, or can be locally stored on a personal computer or the like. The HTML command is typically not displayed when displaying the textual information or the graphical information in the HTML document.

As indicated by block 132, the method includes a step of activating a scent-producing member based on the scent-activating command. The scent-producing member to be activated can be identified within the scent-activating command. Hence, any one or more of a plurality of scent-producing members can be selectively activated using this approach.

Figure 8:
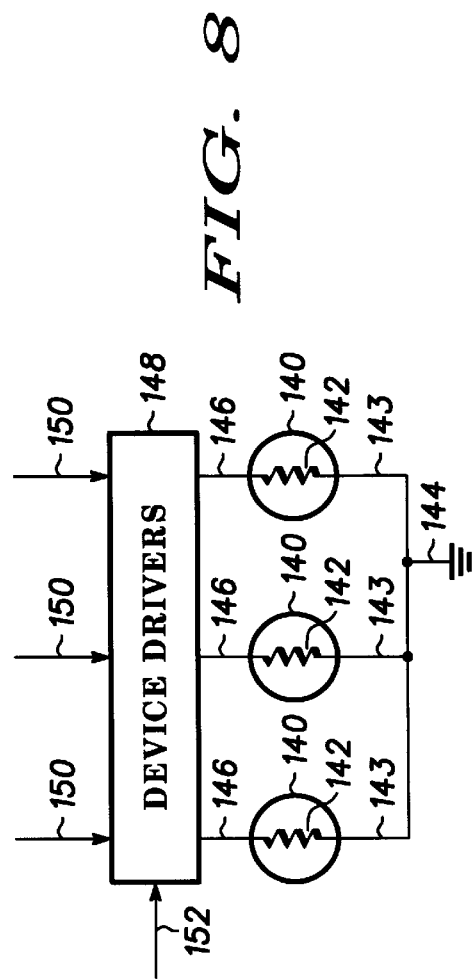
FIG. 8 is a schematic block diagram of an embodiment of a plurality of scent-producing members.

FIG. 8 is a schematic block diagram of an embodiment of a plurality of scent-producing members 140. Associated with each of the scent-producing members 140 is a respective one of a plurality of resistive elements 142. A first terminal 144 of each of the resistive elements 142 is applied to a first voltage line, such as ground 144. Each of the resistive elements 142 has a second terminal 146 applied to a respective one of a plurality of device drivers 148.

The plurality of device drivers 148 can include a plurality of triggers, such as a plurality of transistors. The plurality of device drivers 148 are activated based upon signals received along input lines 150. The plurality of device drivers 148 are powered from a voltage/current applied to a line 152.

Thus, there has been described herein a concept, as well as several embodiments including preferred embodiments of an olfactory card.

Because the various embodiments of the present invention include electronically-activated scent-producing members in a PC card, they provide a significant improvement in augmenting textual, graphical, and audible information with olfactory information. Embodiments of the present invention are amenable for use in advertising applications, promotional applications for fragrances and solvents, and multimedia applications, for example.

Additionally, by including scent-producing members on a member which is removably received and retained by a reusable housing, the scent-producing members can be easily replaced in the olfactory card.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. An olfactory card comprising:
   a PC card housing; and
   a first scent-producing member supported by the PC card housing.

2. The olfactory card of claim 1 further comprising a first electrical component to activate the first scent-producing member.

3. The olfactory card of claim 2 wherein the first electrical component activates the first scent-producing member by heating the first scent-producing member.

4. The olfactory card of claim 2 wherein the first electrical component includes at least one of a resistor and a device having a semiconductor junction.

5. The olfactory card of claim 2 further comprising:

a second scent-producing member; and a second electrical component to activate the second scent-producing member.

6. The olfactory card of claim 5 wherein the first scent-producing member and the second scent-producing member are capable of independent activation.

7. The olfactory card of claim 1 wherein the PC card housing includes a PCMCIA card housing.

8. The olfactory card of claim 1 further comprising a PC card connector supported by the PC card housing.

9. The olfactory card of claim 8 wherein the first scent-producing member is activated in response to a signal received by the PC card connector.

10. The olfactory card of claim 8 further comprising a processor which autonomously activates the first scent-producing member.

11. The olfactory card of claim 8 wherein the PC card connector is supported at a first end of the PC card housing, the PC card housing defining at least one opening at a second end.

12. The olfactory card of claim 11 wherein the at least one opening is for emanating a scent produced by the scent-producing member to an external environment.

13. The olfactory card of claim 1 further comprising a storage medium containing information associated with a scent of the first scent-producing member.

14. The olfactory card of claim 13 wherein the storage medium includes a code indicating when to activate the first scent-producing member.

15. The olfactory card of claim 13 wherein the information includes textual information associated with the scent.

16. The olfactory card of claim 13 wherein the information includes graphical information associated with the scent.

17. The olfactory card of claim 13 wherein the information includes audible information associated with the scent.

18. An olfactory card comprising:

a PC card housing;

a scent-producing member;

an electrical component to activate the scent-producing member;

a PC card connector supported by the PC card housing; and a storage medium in communication with the PC card connector, the storage medium containing at least one of textual information, graphical information, and audible information associated with a scent of the scent-producing member.

19. An olfactory card comprising:

a PC card housing;

a first scent-producing member and a second scent-producing member supported by the PC card housing;

a first electrical component to activate the first scent-producing member;

a second electrical component to activate the second scent-producing member;

a PC card connector supported by the PC card housing; and a storage medium in communication with the PC card connector, the storage medium containing first information associated with a first scent of the first scent-producing member and second information associated with a second scent of the second scent-producing member.

* * * * *